United States Patent [19]
Wilcox

[11] 4,285,010
[45] Aug. 18, 1981

[54] ULTRASONIC INTERROGATING SYSTEM AND EXCITER-DETECTOR CIRCUIT THEREFOR

[75] Inventor: Martin H. Wilcox, Cave Creek, Ariz.

[73] Assignee: Advanced Diagnostic Research Corporation, Tempe, Ariz.

[21] Appl. No.: 845,223

[22] Filed: Oct. 25, 1977

Related U.S. Application Data

[63] Continuation-in-part of Ser. No. 576,874, May 12, 1975, which is a continuation-in-part of Ser. No. 410,437, Oct. 29, 1973, abandoned.

[51] Int. Cl.³ .............................................. H04N 5/30
[52] U.S. Cl. .................................... 358/112; 73/612; 73/626
[58] Field of Search ................. 340/1 R; 73/610, 612, 73/620, 621, 625, 626, 627, 628, 629, 632, 641; 128/2.05 Z; 358/112

[56] References Cited

U.S. PATENT DOCUMENTS

| | | | |
|---|---|---|---|
| 2,852,676 | 9/1958 | Joy | 73/632 |
| 3,086,195 | 4/1963 | Halliday | 340/1 R |
| 3,387,257 | 6/1968 | Brech | 73/610 |
| 3,555,889 | 1/1971 | Weighart | 73/626 |
| 3,672,210 | 6/1972 | Cressman et al. | 73/612 |
| 3,820,387 | 6/1974 | Grabendorfer et al. | 73/67.9 |
| 3,939,696 | 2/1976 | Kossoff | 73/626 |

FOREIGN PATENT DOCUMENTS 2217528 10/1973 Fed. Rep. of Germany.

OTHER PUBLICATIONS

Electro-Scanning Ultrasonic Diagnostic Equipment by Rokuro Uchida, Yoshio Hagiwara & Takasuke Irie, *Japan Medical Electronics* 71/72, pp. 58-62.

*Primary Examiner*—Joseph A. Orsino, Jr.
*Attorney, Agent, or Firm*—Christie, Parker & Hale

[57] ABSTRACT

In order to obviate the necessity for providing a complete channel of electronics for each transducer of an array incorporated into a real-time ultrasonic imaging system, all system transducers are disposed in apparent series with a single inductor as to direct current. Charging resistors permit each transducer to slowly capacitively charge to a predetermined voltage under static conditions. When a switching transistor disposed in series with a given transducer is placed in the conducting state, the transducer rapidly discharges and mechanically deflects to introduce an ultrasonic pulse into an object. While the switching transistor remains conductive, the inductor and transducer are in parallel circuit as to echo signals returning to the transducer. When the switching transistor is rendered non-conductive, the transducer again charges capacitively in anticipation of a succeeding cycle. All echo signals sensed are amplified by a single preamplifier and applied to a display which is sweep coordinated with the sequence of transducer energization.

33 Claims, 8 Drawing Figures

FIG-3 (WILCOX)

ULTRASONIC INTERROGATING SYSTEM AND EXCITER-DETECTOR CIRCUIT THEREFOR

RELATED APPLICATIONS

This application is a continuation-in-part of patent application Ser. No. 576,874, filed May 12, 1975, which is a continuation-in-part of application Ser. No. 410,437, filed Oct. 29, 1973, now abandoned.

BACKGROUND OF THE INVENTION

This invention relates to real-time ultrasonic interrogating systems, and, more particularly, to circuitry for exciting a transducer and for receiving echos in an ultrasonic interrogating system which is for example useful in the biological investigation arts.

A system environment in which the circuitry of the present invention has found significant utility is described in my copending patent application Ser. No. 389,958, for "Ultrasonic Cross-Sectional Imaging System", filed Aug. 20, 1973, and assigned to a common assignee herewith, now Pat. No. 3,881,466. The ultrasonic imaging system disclosed therein is characterized by the use of an array of relatively narrow transducers which are excited in groups according to a predetermined sequence in order to achieve improved resolution by an overlapping ultrasonic scanning pattern.

The most advanced known prior art real-time ultrasonic imaging system for carrying out biological investigations is disclosed in an article by Bom et al, published in the November, 1971, issue of "Bio-Medical Engineering", pages 500-503, 508, and entitled "Ultrasonic Viewer for Cross-Sectional Analyses of Moving Cardiac Structures". The Bom et al apparatus utilizes a linear array of twenty relatively large transducers excited sequentially on an individual basis. Twenty power transistors and twenty preamplifiers are necessary to achieve transducer excitation and echo detection, and the electronic circuits and transducers are coupled by twenty separate coaxial cables. Each transducer is connected in parallel with a tuning inductor, which must be provided to damp unwanted low frequency cross-mode vibrations.

There are two basic disadvantages to the prior art apparatus as exemplified by the Bom et al system. First, the inordinate inherent clumsiness and unreliability are a serious drawback. Second, the necessity for providing twenty complete discrete electronic channels exhibiting high performance characteristics inevitably results in undesirably high costs. The present invention is directed to overcoming both these disadvantages while further affording superior performance.

SUMMARY OF THE INVENTION

It is, therefore, a broad object of my invention to provide improved circuitry for use in a real-time ultrasonic imaging system.

It is another broad object of my invention to provide such improved circuitry in a system especially adapted for use in the medical arts.

It is a more specific object of my invention to provide simplified circuitry which nonetheless exhibits superior performance characteristics in an ultrasonic interrogating system employing a transducer array.

It is also an object of my invention to provide such circuitry in which the necessity for employing a plurality of inductive components and a plurality of echo preamplifiers is obviated thereby affording much lower cost and significantly reduced physical size.

Briefly, these and other objects are achieved as follows. According to one aspect of the invention, a single preamplifier transmits to a display echoes returning to a plurality of ultrasonic transducers. The transducers are selectively excited electrically in a predetermined sequence to produce ultrasonic emission. The respective excited transducers are selectively coupled to the input of the preamplifier in the predetermined sequence in synchronism with the display to present the echoes of the ultrasonic emission on the display. Preferably, the transducers comprise a fixed segmented transducer array having a plurality of discrete adjacent transducer elements, and the preamplifier is packaged with the transducer array.

Another aspect of the invention is a fixed segmented transducer array having a plurality of discrete adjacent transducer elements and a plurality of switches at least equal in number to the transducer elements packaged with the transducer array. The transducer elements are selectively excited electrically in a predetermined sequence to produce ultrasonic emission. Each transducer element is coupled through a respective switch to one end of a common transmission line. The other end of the common transmission line is connected to a display. The switches are selectively closed in the predetermined sequence to transmit to the display via the transmission line echoes of the ultrasonic emission, and the display is synchronized to the switch closures to present the echoes on the display.

Still another aspect of the invention is a plurality of ultrasonic transducers selectively excited to ultrasonic emission in a predetermined sequence, and a single inductive reactance connected effectively in parallel with the respective excited transducers as to echoes of the ultrasonic emission. A plurality of switching devices are each connected in series with a unique one of the transducers to form a plurality of switching device/transducer sets. The switching device/transducer sets are connected in parallel with one another. The single inductive reactance in parallel with the switching device/transducer sets is coupled to the input of a receiver, and the switching devices are selectively closed in the predetermined sequence to transmit to the receiver echoes of the ultrasonic emission. Preferably, the transducers comprise a fixed segmented transducer array having a plurality of transducer elements, and the inductor is packaged with the transducer array.

According to another aspect of the invention applicable either to an ultrasonic tranducer array or to a single ultrasonic transducer, the internal capacitance of the transducer is slowly charged to a first potential and then rapidly discharged to a second different potential to excite the transducer to ultrasonic emission. A tuning inductor and the transducer are effectively connected in series as to direct current during the slow charging interval and effectively connected in parallel as to alternating current during the rapid discharging interval. The transducer and tuning inductor in parallel are coupled across the input of a receiver. Preferably, the receiver cyclically displays ultrasonic echoes returned to the transducer during a first period of each cycle without displaying such signals during a second period of each cycle; the first period corresponds to the discharging interval and the second period corresponds to the charging interval.

The subject matter of the invention is particularly pointed out and distinctly claimed in the concluding portion of the specification. The invention, however, both as to organization and method of operation, may best be understood by reference to the following description taken in connection with the accompanying drawings, in which:

DETAILED DESCRIPTION

Figure 1:
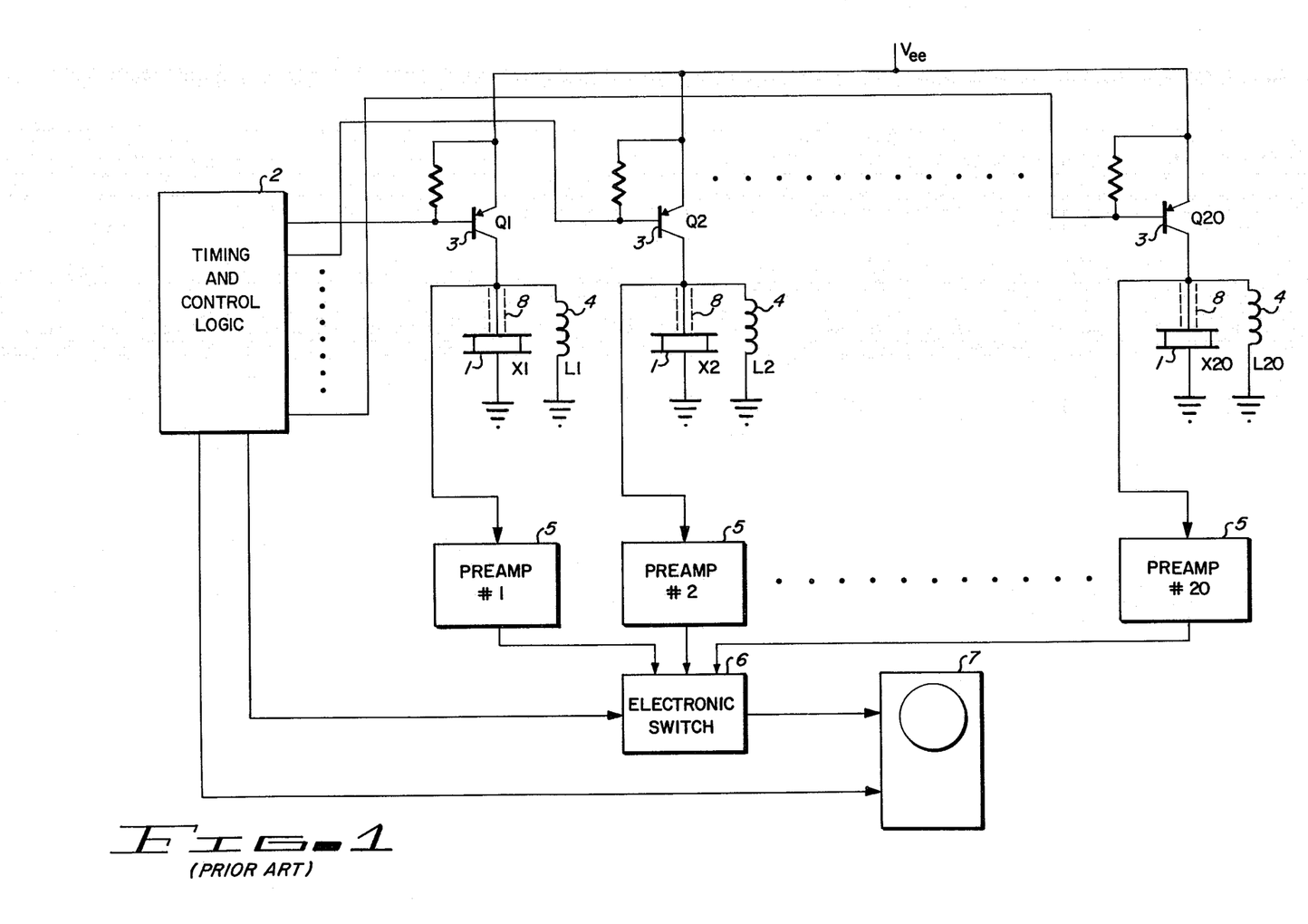
FIG. 1 is a simplified partially schematic and partially block diagram illustrating a circuit configuration exemplary of the prior art.

Referring now to FIG. 1, it will be observed that a twenty-transducer system is depicted by showing only channels 1, 2 and 20, with channels 3-19 omitted to avoid cluttering the diagram. Each transducer 1 is energized by applying an "on" pulse from timing and control logic 2 to the base electrode of an appropriate one of the power transistor switches 3. Any echo received applies a mechanical exertion on the transducer 1 which causes a low level voltage signal to be developed across the transducer and parallel tuning inductor 4. This echo signal is amplified to a useful level by the corresponding preamplifier 5.

An electronic switch 6, under control of the timing and control logic 2, passes the selected echo signals amplified by the preamplifier to a raster scanned display 7 which also receives coordinating signals from the timing and control logic 2. Thus, as the transducers 1 are pulsed in a step-by-step sequence, the echo signals may be observed on the display 7 in a correspondingly time-dependent display to provide a two-dimensional dynamic representation of an organ or area under analysis.

It should be noted that conductors 8 are coaxial cables which are used to couple the electronics to the transducer array which might typically be laid over the chest of a subject under examination or treatment. The aforementioned clumsiness and unreliability in such an environment is particularly undesirable.

Figure 2:
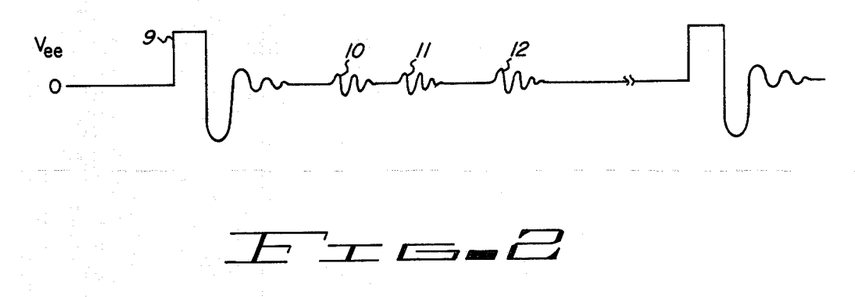
FIG. 2 is a waveform diagram showing a signal observed at a reference point in the circuit of FIG. 1.

FIG. 2 illustrates an exemplary waveform observed at the junction A of a transducer 1, tuning inductor 4, and collector electrode of a transistor switch 3. When an "on" pulse is applied to the base electrode of a given transistor switch 3, V is applied as a pulse 9 across the transducer 1 and inductor 4 coupled to the transistor switch. The consequent mechanical deformation of the transducer introduces a shock wave into the biological subject. As the shock wave propagates through the subject, certain targets reflect echo pulses which deform the transducer 1 to generate echo signals 10, 11 and 12. The amplified and processed echo pulses are applied to a Z-axis input of raster scanned display 7 to modulate the intensity along a scan line corresponding to the specific transducer currently active.

Figure 3:
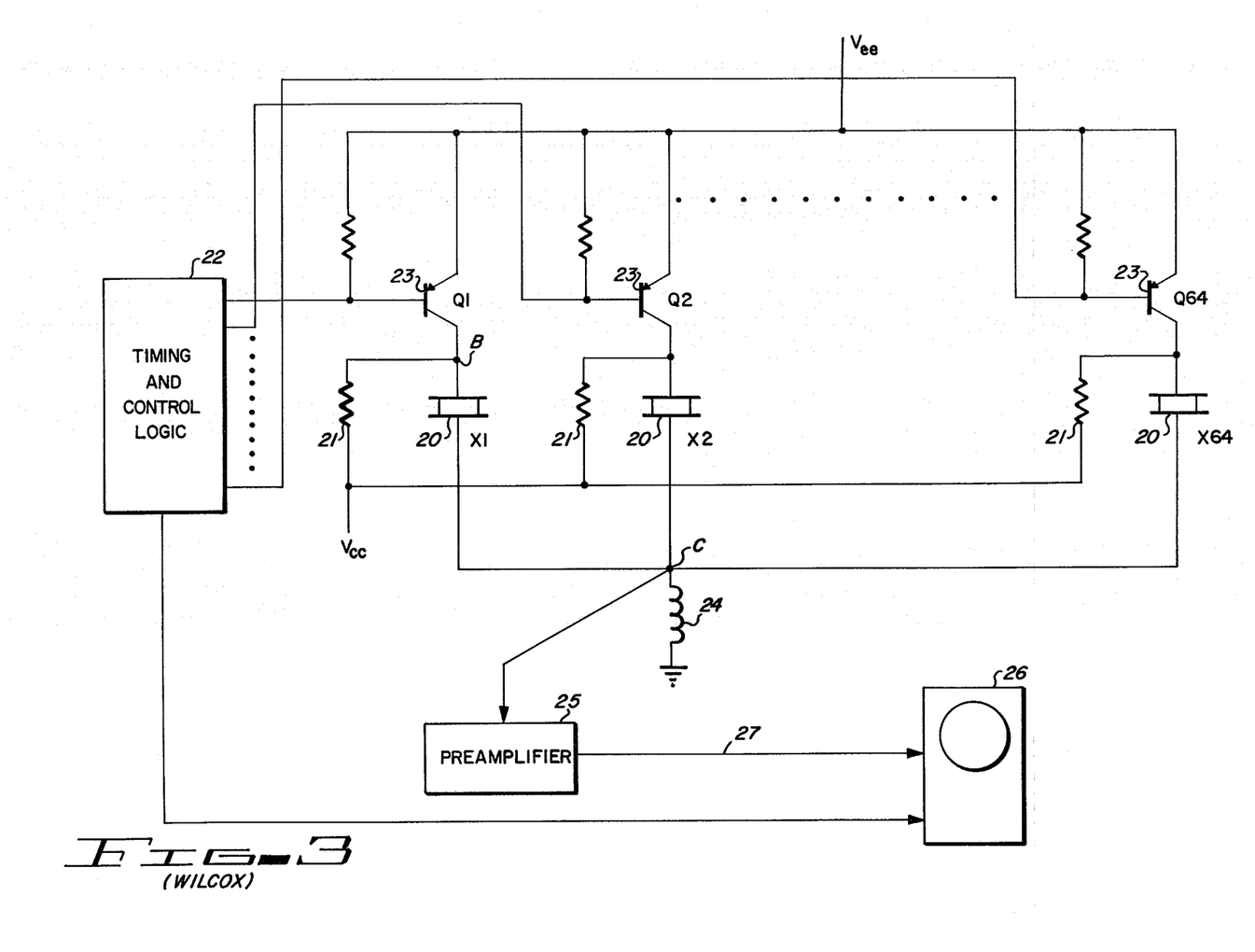
FIG. 3 is a partially schematic and partially block diagram of a circuit configuration comprising one preferred embodiment of the invention.

Referring now to FIG. 3, one preferred embodiment of the subject invention is depicted incorporated into a system in accordance with the referenced U.S. Pat. No. 3,881,466.

A significant feature in the referenced system is the sequence and combinations by which the transducers 20 are excited. A typical transducer array comprises a fixed, segmented transducer array of N discrete adjacent transducer elements. A counter-selector means simultaneously transmits a pulsed electrical signal to A selected adjacent transducer elements of the array and sequentially pulses selected different groups of A contiguous elements, each of which are longitudinally displaced along the elongate array. Each such group is displaced B transducer elements from the location of the immediately preceding group. In the presently preferred system embodiment, $N=64$, $A=4$ and $B=1$. Thus, transducers $X_1$, $X_2$, $X_3$ and $X_4$ are pulsed as a group in unison; then transducers $X_2$, $X_3$, $X_4$ and $X_5$ are pulsed as a group; $X_3$, $X_4$, $X_5$ and $X_6$ are pulsed as a group, etc. The result is an overlapping ultrasonic scanning pattern. With this sequence and combination, the mechanical power, and consequently the electrical power, required of each transducer is much less than required of the individually pulsed prior art system transducers. Consequently, the necessity for using physically large power switching transistors is eliminated. The elimination of the power transistors and the further elimination, by the present invention, of multiple inductors and preamplifiers results in a compact and relatively simply system which exhibits improved performance characteristics. The timing and control logic 22 for effecting the sequential energization of the transducer groups may be of a number of different types which are well known in the art, such as ring counters, shift registers, or more complex binary digital counters. The particular type of circuit used is primarily a design consideration. For example, one type of circuit which could be used to effect the pulsing of these transducers is a shift register pulsing circuit of the type disclosed in the patent to Wendt et al U.S. Pat. No. 3,373,602 issued Mar. 19, 1968.

Figure 4A:
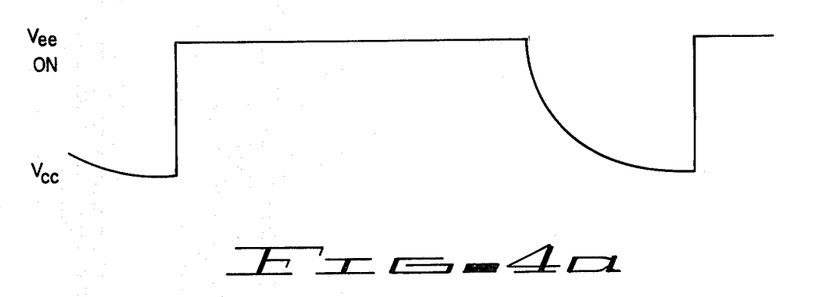
FIGS. 4a and 4b are waveform diagrams showing time related signals observed at two reference points in the circuit of FIG. 3.

Still referring to FIG. 3 and also to FIG. 4a, all transducers 20 will initially capacitively charge to $V_{cc}$ (which is opposite in polarity from $V_{ee}$) through charging resistors 21. Transducers 20 are each connected in series with a respective switching transistor 23 to form a series set. When timing and control logic 22 issues "on" pulses to the base electrodes of the switching transistor 23 in a group of four channels, the switching transistors become conductive and discharge the charge stored on the transducers 20 to $V_{ee}$, as shown in FIG. 4a, electrical point B. The leading edge of the step-like voltage change transiently appearing across the transducers produces a sharp unison mechanical deformation which introduces a highly damped short ultrasonic pulse into the biological subject being analyzed. When the "on" signal is removed from the switching transistors 23, the capacitive charging phase is reestablished in preparation for the next subsequent operating cycle. The capacitance of each of the transducers 20 is considerably smaller than that of the transducers 1 of the prior art apparatus, FIG. 1, by virtue of their smaller physical size. Thus, by appropriately selecting the value of charging resistors 21, the transducers 20 will have adequate time to recharge to $V_{cc}$ before a succeeding "on" pulse again causes discharge.

During the recharging phase of an operating cycle, the mechanical deformation of the transducers will be smoothly relaxed such that all ultrasonic shock waves introduced into the biological subject result only from the discharging phase.

To summarize as depicted in FIG. 4a, the internal capacitance of the respective transducers 20 is cyclically charged and discharged—the respective transducers 20 are first slowly charged through the respective charging resistors 21, to the potential difference between $V_{cc}$ and ground, and then, as the respective switching transistors 23 are closed by an "on" pulse, such internal capacitance is rapidly discharged to the potential between $V_{ee}$ and ground. The rapid discharge of the internal capacitance caused by switch closure excites the discharged transducers to produce ultrasonic emission. After the rapid discharge of the transducer internal capacitance, the corresponding switches remain closed during the interval in which echoes of the ultrasonic emission returned to the transducers are to be sensed. Thus, in this, the preferred embodiment of the invention, the transducers are excited to produce ultrasonic emission by the rapid discharge of their internal capacitance upon switch closure. The terms "charge" and "discharge" as used herein are interchangeable, depending upon what is arbitrarily taken as the starting point of the cycle. Starting from $V_{ee}$, the internal capacitance of the transducer is slowly charged to $V_{cc}$ and rapidly discharged to $V_{ee}$. Starting from $V_{cc}$, the internal capacitance of the transducer is rapidly charged to $V_{ee}$ and slowly discharged to $V_{cc}$.

Figure 4B:
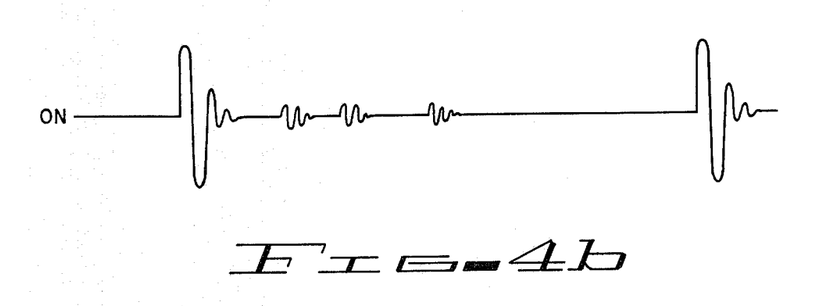

It will be noted that as long as an "on" pulse holds a switching transistor 23 in the conducting state, the terminal of the transducer 20 connected to the collector electrode thereof (electrical point B) is effectively clamped to a-c ground. Thus, as shown in FIG. 4b, returning echoes which cause further mechanical strain in the transducer 20 may readily be sensed at the other transducer terminal (electrical point C) to which one end of an inductive reactance, shown as a single tuning inductor 24, is connected. This electrical point is common to all channels such that only a single preamplifier 25 is needed. The other end of the tuning inductor 24 is connected to ground such that, insofar as echoes are concerned, it is disposed in parallel with the group of those transducers 20 which have switching transistors in the conducting state. Thus tuning inductor 26 is shared by the different groups of transducers as they become operative, i.e., as the switching transistors for such transducers close. Further, the switching transistors for the transducers in the preferred embodiment perform three functions—namely, selecting the transducers to be excited to ultrasonic emission, initiating excitation of the selected transducers to ultrasonic emission, and coupling to the preamplifiers only the echoes returned to the selected transducers.

It should be noted that although inductor 24 is connected effectively in parallel with the group of selected transducers (i.e., the transducers whose switching transistors are in the conducting state) as to alternating current (i.e., tht echoes returned to the transducers), inductor 24 is connected effectively in series with the non-selected transducers 20 (i.e., those having switching transistors in the non-conducting state) as to direct current (i.e., the charging and discharging current furnished by $V_{ee}$ and $V_{cc}$). Consequently, inductor 24 does not short-circuit transducers 20, which would inhibit their charging and discharging in the described manner.

Echoes amplified by the preamplifier during conduction of transistors 23 are coupled by a transmission line designated 27 in FIG. 3, to the raster scanned display 26. These echoes are presented on the display 26 which receives control signals for coordinating scanning from timing and control logic 22.

Figure 5:
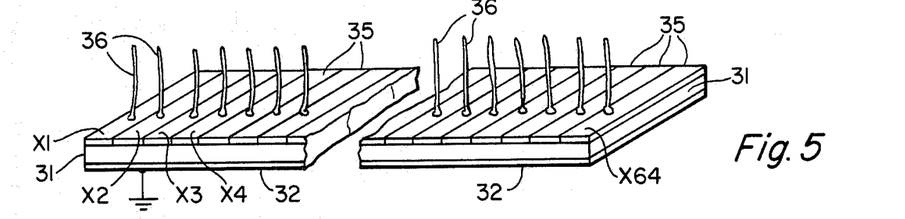
FIG. 5 shows a typical transducer array with which the embodiments of the invention may be used.
Figure 6:
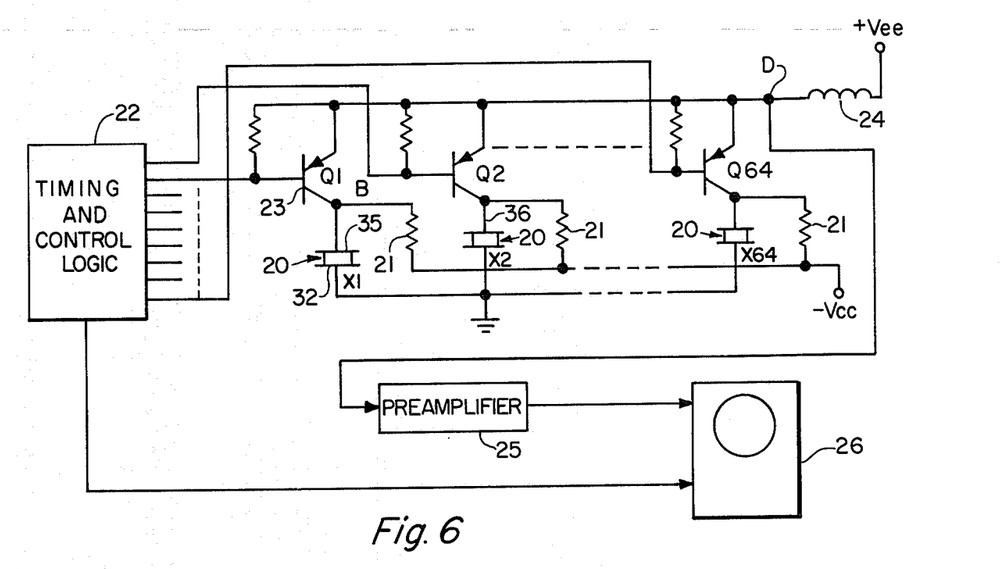
FIG. 6 is a partially schematic and partially block diagram of a circuit configuration comprising another preferred embodiment of the invention.

Referring now to FIG. 5, there is shown a typical transducer array which can be used in conjunction with the circuit of FIG. 3 and the circuit of FIG. 6 to form the various transducers X1 through X64. This array is made in accordance with the array disclosed in U.S. Pat. No. 3,881,466 and comprises a central layer formed of a single piece of suitable transducer material, such as piezoelectric crystal 31. A common conductive electode 32 covers the lower surface of the transducer 31 and the upper surface is covered with adjacent individual conductive strips 35. Each of the strips 35 are separated or are insulated from one another, so that they are electrically independent of one another. This creates a a plurality of electrically independent transducer elements in the array of FIG. 5 which can be separately excited by applying a direct current potential to selected ones of the strips 35 through appropriate input leads 36.

In FIG. 6, there is shown another embodiment of the invention in which the same reference numbers used in FIG. 3 are used to identify the same or similar components. Essentially, the circuit of FIG. 6 operates in the same manner as described previously in conjunction with the operation of the circuit of FIG. 3. In the embodiment shown in FIG. 6, however, the lower or common electrode 32 of the transducers 20 is connected directly to ground instead of being connected through the inductor 24 to ground as shown in the embodiment of FIG. 3. This is the side of the transducer array which is placed against the patient's body over the organ or area under analysis.

The circuit of FIG. 6 then further differs from the circuit of FIG. 3 in that the tuning inductor 24 is connected in series between the $V_{ee}$ positive voltage input terminal and a common point D connected to the emitters of all of the PNP switching transistors 23. In the embodiment shown in FIG. 3, the positive voltage supply terminal $V_{ee}$ is connected directly to the emitters of these transistors. The final difference between the circuit of FIG. 6 and that of FIG. 3 is that the input to the preamplifier 25 in FIG. 6 is taken from point D, which is the junction of the lower end of the inductor 24 with the emitters of the switching transistors 23.

The timing and control logic circuit 22 sequentially renders different groups of the switching transistors 23 conductive in the same manner described previously in conjunction with the description of the circuit of FIG. 3. The advantages of the circuit of FIG. 3, namely, the elimination of the power transistors and the further elimination of multiple inductors and preamplifiers, also are present in the circuit of FIG. 6.

The circuit of FIG. 6, however, also has the additional advantage of being substantially immune from radio frequency interference (RFI), being coupled to the load from the transducers 20 which are "off" or connected to non-conductive switching transistors 23. In the circuit shown in FIG. 3, all of the transducers 20 have one terminal connected in common to the output terminal of the transducer array supplied to the preamplifier 25. As a consequence, if radio frequency interference is capacitively coupled to an "off" transducer, it is possible for that transducer to capacitively couple the interference to the inductor 24. This spurious signal in turn would be coupled from terminal C to the preamplifier 25 in the same manner as the desired echo pulses from the transducers which are "on" or being driven by pulses from the switching transistors 23. While the circuit of FIG. 3 is a much improved real-time ultrasonic imaging system over systems previously available in the prior art, this disadvantage of the circuit could become a problem if the array were operated in a region subject to substantial radio frequency interference. The circuit array of FIG. 6 is not subject to such interference.

In the circuit of FIG. 6, the common point of the transducers, terminal 32, is connected to ground potential. The other terminal, terminal 35, of each of the transducers is coupled through its corresponding switching transistor 23 to the common terminal D with the inductor 24. Thus, when the corresponding transistor 23 is non-conductive, essentially an open circuit is presented to the transducer 20 with respect to the inductor 24. Thus, no pulses from an "off" transducer 20 can be coupled to the inductor 24 to cause erroneous data to be reproduced by the display 26. The inductor 24 still is connected in a series circuit with the conducting switching transistors 23 and their corresponding transducers 20, as it is in the embodiment shown in FIG. 3. The relocation, however, of the inductor 24 to the positive direct current voltage side of the circuit, rather than the grounded side, i.e., from the side of transistors 23 with transducers 20 to the other side of transistors 23, results in the improved performance noted.

Figure 7:
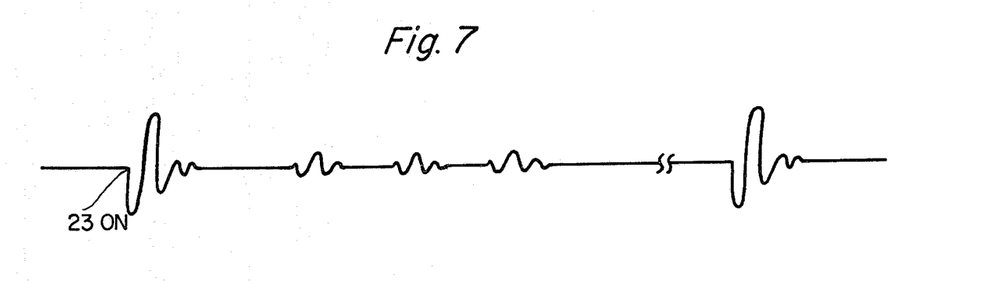
FIG. 7 is a waveform diagram showing time related signals observed at a reference point in the circuit of FIG. 6.

The input for the preamplifier 25 in the circuit of FIG. 6 then is obtained from the common terminal D, which is similar to the terminal C of FIG. 3, except that it is on the positive voltage input side of the system rather than on the grounded side. As a consequence, the pulses applied to the preamplifier 25 from terminal D are reversed in polarity from those obtained from terminal C in the circuit of FIG. 3. These reversed polarity input and echo pulses are shown in FIG. 7. A comparison of FIG. 7 with FIG. 4b shows substantially similar waveforms which are 180° out of phase with one another.

With the exception of the differences noted, the circuit of FIG. 6 operates in the same manner as the circuit of FIG. 3, and both circuits exhibit substantial improvements in ultrasonic imaging systems.

The elimination of power transistors, plural inductors, and plural preamplifiers permits packaging the electronics, i.e., switching transistors 23, tuning inductors 24, and preamplifier 25, directly with the transducer array. Consequently, a very much simplified and more facile physical arrangement is realized, while the above-mentioned objects of the invention are admirably met.

It will be appreciated that other means may be employed to excite the transducers, the same switches still selecting the transducers to be excited and coupling only the echoes returned to the selected transducers to the display, and the single inductor and/or preamplifier still being shared by all the transducers. Further, although the invention has been described as interrogating biological subjects, it is applicable to interrogation of other targets such as objects subject to non-destructive testing. Moreover, plural switches could be provided for each transducer array element if phase controlled focusing is utilized.

Having fully described a presently preferred embodiment of my invention in such terms as to enable those skilled in the art to which it pertains to understand and practice it,

I claim:

1. An ultrasonic interrogating system comprising:
   a plurality of ultrasonic transducers;
   means for selectively exciting the transducers electrically in a predetermined sequence to produce ultrasonic emission;
   raster scanned display means;
   a single preamplifier having an output connected to the display means and an input;
   means for coupling the respective excited transducers to the input of the preamplifier in the predetermined sequence to transmit to the display means echoes of the ultrasonic emission of the respective excited transducers returned to said respective excited transducers;
   a single tuning inductor effectively connected in parallel with the excited transducers as to echoes of the ultrasonic emission; and
   means for synchronizing the display means of the coupling means to present the echoes of the ultrasonic emission on the display means.

2. The system of claim 1, in which the plurality of ultrasonic transducers comprises a fixed segmented transducer array having a plurality of discrete adjacent transducer elements and the preamplifier is packaged with the transducer array.

3. An ultrasonic interrogating system comprising:
   a fixed segmented transducer array having a plurality of discrete adjacent transducer elements;
   means for selectively exciting the transducer elements to ultrasonic emission in a predetermined sequence;
   a raster scanned display;
   a plurality of switches equal in number to the transducer elements packaged with the transducer array;
   a common transmission line having a first end and a second end;
   first means for coupling each transducer element responsive to a respective switch when closed to the first end of the transmission line;
   second means for coupling the second end of the transmission line to the display;
   means for selectively closing the switches in the predetermined sequence to transmit to the display via the transmission line echoes of the ultrasonic emission of the respective excited transducers returned to said respective excited transducers;
   a single tuning inductor packaged with the transducer array;
   means for connecting the single tuning inductor effectively in parallel with the respective excited transducer elements as to echoes of the ultrasonic emission; and
   means for synchronizing the display to the switch closing means to present the echoes on the display.

4. The system of claim 3, in which the first coupling means includes a single preamplifier packaged with the transducer array.

5. An ultrasonic imaging system comprising:
   a single inductive reactance;
   a plurality of transducers;

a plurality of switching devices each connected in series with a unique one of the transducers to form a plurality of series sets;

means for electrically connecting the plurality of series sets in parallel with one another;

means for selectively exciting the transducers electrically in a predetermined sequence to produce ultrasonic emission;

means for connecting the single inductive reactance effectively in parallel with the plurality of series sets as to echoes of the ultrasonic emission;

a receiver having an input across which the single inductive reactance in parallel with the series sets is coupled; and means for selectively closing the switching devices in the predetermined sequence to transmit to the receiver echoes of the ultrasonic emission of the respective transducers returned to said respective transducers.

6. The system of claim 5, in which the plurality of transducers comprises a fixed segmented transducer array having a plurality of discrete adjacent transducer elements and the single inductive reactance comprises a tuning inductor packaged with the transducer array.

7. The system of claim 6, in which the transducer array comprises a single piece of piezoelectric material having a first and second opposite surfaces, a common conductive electrode covering the first surface of the piezoelectric material, and a plurality of adjacent insulated conductive strips equal in number to the transducer elements covering the second surface of the piezoelectric material, the strips are connected to the respective switching devices, and the common electrode is grounded.

8. The system of claim 5, in which the means for selectively exciting the transducers comprises means upon closure of each switching device for exciting the corresponding transducer electrically to produce ultrasonic emission.

9. The system of claim 8, in which the transducers each have an internal capacitance and the means upon closure of each switching device for exciting the corresponding transducer electrically comprises:

means prior to closure of each switching device for slowly charging the internal capacitance of the corresponding transducer to be excited; and means upon closure of each switching device for rapidly discharging the internal capacitance of said corresponding transducer to excite it electrically to produce ultrasonic emission.

10. The system of claim 9, in which the means for charging the internal capacitance of the corresponding transducer comprises a shared direct current voltage source having first and second output terminals, a charging resistor connected in series between the first output terminal of the source and the junction between the switching device and the respective transducer, and means for connecting the second output terminal of the source to the single inductive reactance and the plurality of series sets to complete a charging circuit for the transducer between the first and second output terminals of the source without short circuiting the internal capacitance of the transducers by the inductive reactance.

11. The system of claim 10, in which the means for discharging the internal capacitance of the respective transducers comprises a common node at a potential different from the potential across the first and second output terminals, and means for connecting the common node to the single inductive reactance and the plurality of series sets to complete a discharging circuit for the transducers to the potential at the common node when the respective switching devices are closed.

12. The system of claim 5, in which the receiver includes a raster scan display producing scan lines corresponding to said respective transducers, means for modulating the intensity of the scan lines responsive to the echoes returned to the corresponding transducers, and means for synchronizing the scan lines to the closing means.

13. The system of claim 5, in which the plurality of transducers comprises N discrete adjacent transducer elements, and the closing means comprises means for simultaneously closing the switching devices connected in series with a selected group of A adjacent transducer elements and means for sequentially displacing the selected group of A transducer elements B transducer elements from the preceeding group in the sequence.

14. The system of claim 13, in which B is one.

15. The system of claim 13, in which A is four and N is sixty-four.

16. An ultrasonic interrogating system comprising:

an ultrasonic transducer having internal capacitance;

a charging resistor connected in series with the transducer to form therebetween a junction;

a first circuit node at a first direct current potential coupled to the charging resistor and transducer in series to slowly change the potential at the junction through the charging resistor toward the first direct current potential;

a second circuit node at a second direct current potential different from the first potential;

normally open switching means coupling the junction of the charging resistor and the transducer to the second circuit node;

means for closing the switching means to change the potential at the junction rapidly toward the second potential to excite the transducer electrically to produce ultrasonic emission;

a tuning inductor;

means for connecting the tuning inductor effectively in parallel with the transducer as to echoes of the ultrasonic emission returned to the transducer, without short-circuiting the internal capacitance of the transducer by the inductor as to direct current;

a receiver having an input; and means for coupling the transducer and the tuning inductor effectively in parallel as to echoes of the ultrasonic emission across the input of the receiver.

17. The system of claim 16, additionally comprising a first source of direct current voltage having first and second output terminals across which a potential difference appears, the first output terminal of the first source being connected to the first circuit node and the second output terminal of the first source being connected to ground; and a second source of direct current voltage having first and second output terminals across which a potential difference appears, the first output terminal of the second source being connected to the second circuit node and the second output terminal of the second source being connected to ground.

18. The system of claim 17, in which the first and second potentials have different polarities.

19. The system of claim 16, in which the switching means operates cyclically, the switching means being open during a first interval of each operating cycle, and the receiver includes a display having a scan line with an intensity modulated by the single applied to the input of the receiver and means responsive to the switching means for synchronizing the scan line of the display to the closures of the switch.

20. An ultrasonic interrogating system comprising:
an ultrasonic transducer having an internal capacitance;
means for cyclically displaying ultrasonic echoes received by the transducer during a first period of each cycle without displaying such signals during a second period of each cycle;
means for slowly charging the internal capacitance of the transducer to a first potential during the second period of each cycle;
means for rapidly discharging the internal capacitance of the transducer to a second potential different from the first potential during the first period of each cycle to excite the transducer to ultrasonic emission;
a tuning inductor; and
means for connecting the transducer and the tuning inductor effectively in series as to direct current during the second period of each cycle and for connecting the transducer and the tuning inductor effectively in parallel as to alternating current during the first period of each cycle.

21. An exciter-detector circuit for use in an ultrasonic imaging system including in combination:
at least first and second voltage supply terminals;
an inductive reactance;
a plurality of transducers;
a plurality of switching devices, each connected in series with a unique one of said transducers to form a plurality of series sets;
means for electrically connecting said series sets in parallel with one another and in series with said inductive reactance across said first and second voltage supply terminals; and
an output terminal coupled with said inductive reactance at a junction thereof with said series sets.

22. An exciter-detector circuit particularly adapted for use in a real-time ultrasonic imaging system which includes sequential activating means and raster scanned display means, said circuit including in combination:
a plurality of sequentially activated transducers, each of said transducers having first and second terminals;
at least first and second voltage supply terminals;
a plurality of switching means each having first, second, and control electrodes, the first electrodes of said switching means being coupled in circuit with a first common electrical point, and the second electrode of each of said switching means being coupled with the first terminal of a unique one of said transducers;
means for coupling said first voltage supply terminal with the first common electrical point;
a plurality of resistors, each resistor being coupled between said second voltage supply terminal and the first terminal of a unique one of said transducers;
means for coupling the second terminals of all said transducers to a second common electrical point;
an inductive reactance having first and second terminals and connected in series circuit common with said plurality of said transducers and said plurality of said switching means, with the first terminal thereof coupled to one of said first and second common electrical points;
means coupled with the control electrodes of said switching means for controlling the conductivity thereof according to a predetermined pattern; and
an output terminal coupled with the one of said first and second common points to which the first terminal of said inductive reactance is coupled.

23. The combination according to claim 22 wherein the first terminal of said inductive reactance is coupled with said second common electrical point and the second terminal thereof is coupled with ground.

24. The combination according to claim 22 wherein said first terminal of said inductive reactance is coupled with said first common electrical point and the second terminal thereof is coupled with said first voltage supply terminal.

25. The combination according to claim 24 wherein said second common electrical point is coupled with ground.

26. The combination according to claim 22 further including a preamplifier having an input coupled with said output terminal and an output for coupling with the raster scan display means.

27. An exciter-detector circuit particularly adapted for use in a real-time ultrasonic imaging system which includes sequential activating means and raster scan display means, said circuit including in combination:
a plurality of sequentially activated transducers, each of said transducers having first an second terminals;
at least first and second voltage supply terminals;
a plurality of switching transistors each having first, second and control electrodes, the first electrodes of said switching transistors being coupled in circuit with a first common electrical point, and the second electrode of each of said transistors being coupled with the first terminal of a unique one of said transducers;
an inductive reactance having first and second terminals, the first terminal being coupled with said first common electrical point and the second terminal being coupled with said first voltage supply terminal;
a plurality of resistors, each said resistor being connected between said second voltage supply terminal and the first terminal of a unique one of said transducers;
means coupling the second terminals of all of said transducers with ground;
means coupled with the control electrodes of said switching transistors for controlling the conductivity thereof according to a predetermined pattern; and
an output terminal coupled with said first common electrical point.

28. The combination according to claim 27, further including a preamplifier having an input coupled with said output terminal and an output for coupling with the raster scan display means.

29. The combination according to claim 28 wherein said first voltage supply terminal is adapted for coupling with a source of positive direct-current voltage; said second voltage supply terminal is adapted for connection with a source of negative direct-current voltage; and said switching transistors are PNP transistors with said first, second and control electrodes corresponding respectively to emitter, collector and base electrodes thereof.

30. An exciter-detector circuit specially adapted for use in a real-time ultrasonic imaging system which includes sequential activating means and raster scan display means, said circuit comprising:
- a plurality of sequentially activated transducers, each of said transducers having first and second terminals;
- a first voltage source of a first polarity;
- a second voltage source of a second polarity;
- a plurality of switching transistors, each said switching transistor being connected between said first voltage source and said first terminal of a unique one of said transducers;
- a plurality of resistors, each said resistor being connected between said second voltage source and said first terminal of a unique one of said transducers;
- means connecting said second terminals of all said transducers to a common electrical point;
- an inductor connected between said common electrical point and ground; and
- a preamplifier having an input connected to said common electrical point and an output for coupling to said display means.

31. An exciter-detector circuit for use in an ultrasonic imaging system including in combination:
- at least first and second voltage supply terminals;
- an inductive reactance;
- a plurality of transducers;
- a plurality of switching devices, each connected in series with a unique one of said transducers to form a plurality of series sets;
- means for electrically connecting said series sets in parallel with one another across said first and second voltage supply terminals;
- means for coupling said inductive reactance between one of said voltage supply terminals and a common junction of said series sets; and
- an output terminal coupled with said inductive reactance at said common junction.

32. The circuit of claim 31, additionally comprising a third voltage supply terminal, a plurality of charging resistors equal in number to the transducers, connected between the third voltage supply terminal and the junctions between the respective transducers and switching devices such that the voltage at said junctions changes rapidly when the respective switching devices are closed.

33. The circuit of claim 32, additionally comprising means for selectively closing the switching devices in a predetermined sequence.

* * * * *